(12) United States Patent
Pastl

(10) Patent No.: US 10,709,486 B2
(45) Date of Patent: Jul. 14, 2020

(54) BONE SCREW

(71) Applicant: Klaus Pastl, Lichtenberg (AT)

(72) Inventor: Klaus Pastl, Lichtenberg (AT)

( * ) Notice: Subject to any disclaimer, the term of this patent is extended or adjusted under 35 U.S.C. 154(b) by 113 days.

(21) Appl. No.: 15/566,056

(22) PCT Filed: Mar. 30, 2016

(86) PCT No.: PCT/AT2016/050084
§ 371 (c)(1),
(2) Date: Oct. 12, 2017

(87) PCT Pub. No.: WO2016/164946
PCT Pub. Date: Oct. 20, 2016

(65) Prior Publication Data
US 2018/0125553 A1    May 10, 2018

(30) Foreign Application Priority Data
Apr. 15, 2015   (AT) .............................. A 50301/2015

(51) Int. Cl.
*A61B 17/86* (2006.01)
*A61F 2/28* (2006.01)
*A61B 17/00* (2006.01)

(52) U.S. Cl.
CPC ........ *A61B 17/8625* (2013.01); *A61B 17/866* (2013.01); *A61B 17/863* (2013.01); *A61B 17/8605* (2013.01); *A61B 17/8645* (2013.01); *A61B 2017/00933* (2013.01); *A61F 2/28* (2013.01)

(58) Field of Classification Search
CPC ......... A61B 2017/00933; A61B 17/866; Y10S 606/909; A61F 2002/2838
See application file for complete search history.

(56) References Cited

U.S. PATENT DOCUMENTS

| | | | | |
|---|---|---|---|---|
| 5,584,836 A | * | 12/1996 | Ballintyn | A61B 17/0401 606/232 |
| 5,824,079 A | * | 10/1998 | Siegler | A61B 17/0401 128/898 |
| 5,868,749 A | * | 2/1999 | Reed | A61B 17/80 606/104 |
| 6,099,529 A | * | 8/2000 | Gertzman | A61B 17/8605 606/309 |
| 6,162,225 A | * | 12/2000 | Gertzman | A61B 17/861 606/309 |

(Continued)

*Primary Examiner* — David W Bates
(74) *Attorney, Agent, or Firm* — Underwood & Associates, LLC

(57) ABSTRACT

A bolt with an external thread and a cylindrical bolt shank made of allogeneic, cortical bone material for surgically operative osteosynthesis, wherein the external thread concerns a symmetrical angular or trapezoidal thread which has at least one thread turn per millimeter, and the bone material is formed by osteons (5) and is permeated by Haversian canals (6). According to the invention, it is proposed that the thread flanks (9a, 9b), delimiting a thread groove of the angular or trapezoidal thread merge into one another via a thread root portion (8) whose length, in an axial section of the bolt, is in the range of 0.02 mm to 0.6 mm. In this way, it is possible to produce bone screws (1) with increased strength, such that less suitable donor material can also be used for the production of high-quality bone screws (1).

6 Claims, 2 Drawing Sheets

(56) References Cited

U.S. PATENT DOCUMENTS

| | | | | |
|---|---|---|---|---|
| 7,122,037 B2* | 10/2006 | Happonen | A61B 17/86 | 606/308 |
| 7,194,314 B1* | 3/2007 | Richter | A61N 1/36036 | 600/25 |
| 9,011,505 B2* | 4/2015 | Prandi | A61B 17/863 | 411/387.8 |
| 9,173,692 B1* | 11/2015 | Kaloostian | A61B 17/8685 | |
| 2002/0016595 A1* | 2/2002 | Michelson | A61B 17/8605 | 606/301 |
| 2002/0052605 A1* | 5/2002 | Grooms | A61B 17/862 | 623/13.14 |
| 2002/0123751 A1* | 9/2002 | Fallin | A61B 17/68 | 606/331 |
| 2007/0010820 A1* | 1/2007 | Contiliano | A61B 17/0401 | 606/86 A |
| 2008/0215060 A1* | 9/2008 | Garcia | A61B 17/86 | 606/104 |
| 2010/0023064 A1* | 1/2010 | Brunger | A61B 17/8605 | 606/308 |
| 2011/0144766 A1* | 6/2011 | Kale | A61B 17/686 | 623/23.63 |
| 2014/0350608 A1* | 11/2014 | Goel | A61B 17/8685 | 606/279 |
| 2015/0133934 A1* | 5/2015 | Felfel | A61L 31/128 | 606/60 |
| 2017/0189090 A1* | 7/2017 | Champagne | A61B 17/7291 | |
| 2018/0199969 A1* | 7/2018 | Kim | A61B 17/7032 | |
| 2019/0307496 A1* | 10/2019 | Pastl | A61B 17/866 | |

\* cited by examiner

BONE SCREW

The invention relates to a bolt with an external thread and a cylindrical bolt shank made from allogeneic, cortical bone material for surgically operative osteosynthesis, wherein the external thread concerns a symmetrical angular or trapezoidal thread, which has at least one thread turn per millimeter, and the bone material is formed by osteons and with Haversian canals, according to the preamble of claim 1.

If the external thread of such a bolt extends over the entire longitudinal extension of the bolt, it is also possible to speak of a threaded pin. If the bolt is also provided with an unthreaded head, reference can also be made to a bone screw. In the following, reference will be made preferably to bone screws, which shall also include embodiments in the form of a threaded pin.

Bone screws for surgically operative osteosynthesis are conventionally made of metal or metal alloys. Furthermore, bone screws of resorbable material such as polyglycolide and polylactide are known, as well as screws of xenogeneic bone. However, bone screws of this type have several disadvantages in surgical practice. On the one hand, screws made of metal or metal alloys must be removed again by a second operation for example, and on the other hand are subject to changes by corrosion. This increases the costs in the health system. In addition, there is an additional health risk for each patient through a new operation that does not occur in allogeneic bone screws. Although all resorbable materials in the human or animal body, depending on the material, again form a more or less firm bridge between the osteosynthesizing bones, they are dissolved, which adversely affects the strength of the osteosynthesis of the affected bones. Furthermore, some resorbable osteosynthesis materials lead to great osteolyses in the surrounding bone during their degradation, i.e. a yielding away of the receiver bone from the screw. Xenogenic (species-foreign) materials in turn result in rejection reactions and are also unsuitable for osteosynthesis because they are not incorporated into the surrounding recipient bones, but are rejected and degraded, even if the protein in the bone was previously denatured by heat. Furthermore, the different modulus of elasticity of bovine corticalis and human corticalis (human approx. 16,000 N/mm$^2$, beef approx. 22,000 to 24,000 N/mm$^2$) helps human tissue to heal much better. The shape retention and modulus of elasticity of the cortical bone are species-dependent.

Allogeneic bone screws (femur and tibial corticalis) on the other hand offer several advantages. They are vascularized and reconstructed without a rejection reaction, and are particularly suitable for osteosyntheses where small bone fragments must be joined, since the screw produces a supporting bone bridge already during the operation which improves from the time of the operation by rebuilding and being fully integrated into the living bone. In contrast, metal screws represent rather an obstacle to bone regeneration, in particular they reduce the available surface which would be present for bone healing by their mere presence. Degradable materials, in turn, have their maximum strength at the time of surgery. For them the same disadvantages apply as for the metal screws. Furthermore, the strength rapidly decreases as soon as the degradation process occurs, as a result of which the bone site to be osteosythesized is at least temporarily weakened again.

Furthermore, in bone screws of allogeneic bone, a second operation for the removal of the osteosynthesis material can be omitted since the bone is completely converted into own bone (not resorbed!). For the patient, therefore, the operational risk is reduced, thus inevitably decreasing the costs for the health care system. Screws of allogeneic bone also do not interfere with the application of imaging techniques, as opposed to metal screws, which leave disturbing artefacts in MRI and CT. Also, follow-up examinations are possible without any problem, and allow a better assessment of the healing success.

Bone screws suitable for surgical practice have been described, for example, in the specifications EP 2384712 B1 and WO 2013/164106 A1 of the applicant, which is also referred to below as the closest prior art. The bone screws described therein have, in particular, a bolt shank provided with an external thread, wherein the external thread is a symmetrical angular or trapezoidal thread which has at least one thread turn per millimeter. The symmetrical angular or trapezoidal thread has the advantage that the flank of a thread turn facing the screw-in direction has the same angle as its remote flank. Therefore, it does not exert any pulling action on the bone. In the course of operative osteosynthesis, the fixation and compression of the bone parts to be joined is first ensured by appropriate surgical instruments. Subsequently, a core bore is placed into which a thread is cut. The bone screw can now be inserted, wherein the bone screw holds the bone parts in a stable state with a predetermined distance, without thereby exerting a compression, since a symmetrical angular or trapezoidal thread hardly permits tensile loads. Such a bone screw therefore does not constitute a tensile screw. The pressure load on the nut thread and on the screw thread is reduced, or at least equally distributed to both thread sections due to the symmetrical flank angle. Thus, pressure necroses of the bone can be prevented or counteracted in this manner in the best possible way. Owing to the high thread count of at least one thread turn per millimeter and the resulting frictional forces, this also results in a high rotational stability of the bone screw and above all a large surface for bone healing.

For an applicability of screws from allogeneic bone, however, it is also necessary in particular to optimize them with regard to screw-in resistance and strength. Bone screws from allogeneic, human corticalis are very brittle in nature and can easily break during torsion and tensile loads. However, stresses on the bone screw do not only occur during the insertion of the bone screw during the operation but also during the postoperative healing phase. Since the generic bone screws are also obtained from allogeneic human corticalis, the starting material is subject to fluctuating properties which affect the quality of the bone screw made from this starting material. These fluctuations occur not only within one and the same bone, but also in the bone material of different donors. In fact, this is also a reason why screws from autologous or allogeneic bone have so far not been widely used in surgical practice.

That is why embodiments were proposed in the Austrian patent AT 511.943 of the applicant for screws of allogeneic cortical bone in which in a cross-section normal to the longitudinal axis of the bolt shank the total area of the Haversian canals occupies at most 10% of the total area of the cross-section. A Haversian canal is the central bone canal in the middle of an osteon, which is the basic element of the cortical bone. An osteon consists of concentrically arranged lamellae, which are also referred to as special lamellae, a centrally located Haversian canal and the osteocytes lying between the lamellae. Blood vessels, connective tissue cells and fibers, as well as individual nerve fibers, run in the Haversian canal. Osteons and Haversian canals only occur in the cortical bone of long tube bones, wherein the Haversian canals essentially extend in the longitudinal direction of the bone. During the cutting of bone screws, conventionally the symmetry of the bone structure is followed and the bone screw is cut in the longitudinal direction of the donor bone so that the longitudinal axis of the bolt shank extends substantially in the longitudinal direction of the donor bone. Thus, the Haversian canals in the bolt shank also extend essentially in the longitudinal direction of the bolt shank.

As has now been determined by the applicant, the mechanical properties of bone screws from allogeneic, cortical bone material depend to a considerable extent on the available bone matrix. An increase in the area of the Haversian canals in the cross-section of a bone reduces the available bone matrix, wherein the area proportion of the Haversian canals in the bone cross-section varies not only along the length of the bone, but also between the bone material of different donors. The criterion proposed in the Austrian patent AT 511.943 that in a cross-section normal to the longitudinal axis of the bolt shank the total area of the Haversian canals may occupy a maximum of 10% of the total area of the cross-section, represents a simple and easily measurable criterion for the selection of the starting material for the production of bone screws, which ensures a good quality of the bone screw in a reliable manner.

Unfortunately, the proportion of the material which proves to be unsuitable when this criterion is applied proves to be high. Donor bones are, however, a very limited resource, which must be handled with care and with the best possible utilization. It would therefore be desirable to be able to also use material of less suitable donor bones for producing high-quality bone screws.

In other words, it is the object of the invention to realize bone screws of increased strength so that even less suitable donor material can be used for producing high-quality bone screws.

This object is achieved by the features of claim 1. Claim 1 relates to a bolt with external thread and a cylindrical bolt shank made of allogeneic, cortical bone material for surgically operative osteosynthesis, wherein the external thread is a symmetrical angular or trapezoidal thread, which has at least one thread turn per millimeter, and the bone material is formed by osteons and permeated by Haversian canals. According to the invention, it is provided in this case that the thread flanks of the symmetrical angular or trapezoidal thread, which delimit a thread groove, pass into one another via a thread root portion, whose length, in an axial section of the bolt, lies in the range from 0.02 mm to 0.6 mm. With the aid of a thread root portion arranged in accordance with the invention, the fracture strength of a bone screw can be increased by more than 30%, as the applicant's experiments have shown. This surprisingly strong effect can not be attributed to the mere avoidance of tension peaks, as is the desirable in mechanics when designing components. The effect of this significant increase in the fracture strength of bone screws with fine threads is instead attributed by the applicant to the structure of the bone material used. The lengths of the thread root portion specified in the interval provided according to the invention are in the range of the dimensions of the structural units which are decisive in the bone material, such as, for example, the Haversian canals and the osteons. The interval boundaries defining the interval according to the invention are therefore also comparable with the smallest occurring diameters of Haversian canals (approximately 20 μm) and the largest diameters of the osteons (about 400 μm). In other words, the interval provided according to the invention for the lengths of the thread root portions could also be interpreted such that the thread flanks of the symmetrical angular or trapezoidal thread delimiting a thread root merge into one another via a thread root portion, whose length, in an axial section of the bolt, is above the average diameter of the Haversian canals of the respective bone material and below the average diameter of the osteons of the bone material. The significant increase in the fracture strength is attributed by the applicant to the fact that the thread flanks and the thread root portion connecting the thread flanks intersect the Haversian canals and above all the osteons surrounding them at an increasingly flat angle, the greater the length of the thread root portion is. The interval provided in accordance with the invention can be used in the case of a thread root portion, which is designed as a circular arc, in thread root radii of approximately 0.01 mm to 0.20 mm, which corresponds to 10 μm to 200 μm. In this region the corresponding circular arc has a curvature which is comparable to that of the osteons, which explains the grinding cut. In particular, it would also be conceivable in the case of shorter thread sections, however, to approximate the circular arc by a linear section, so that the two thread flanks in each case converge via an edge into the thread root portion. Preferably, however, it is provided that the transition of the thread flanks into the thread root portion occurs in each case in an edge-free manner. In the case of loading, the pressure acting on the thread flanks and the thread root portion of the bone screw is respectively distributed evenly over the entire tissue of the bone material, i.e. to many surrounding osteons. Tensile and compressive loads are thus transferred uniformly and without stress and are distributed to the bone material over a larger area. This makes it possible for even lower quality, more porous bone material to be used for the production of bone screws with equivalent fracture strength.

In practice, thread root radii of 0.08 mm to 0.20 mm, preferably 0.12 mm, have proven successful.

The invention will be explained in more detail below with reference to the accompanying drawings, wherein.

Figure 1:
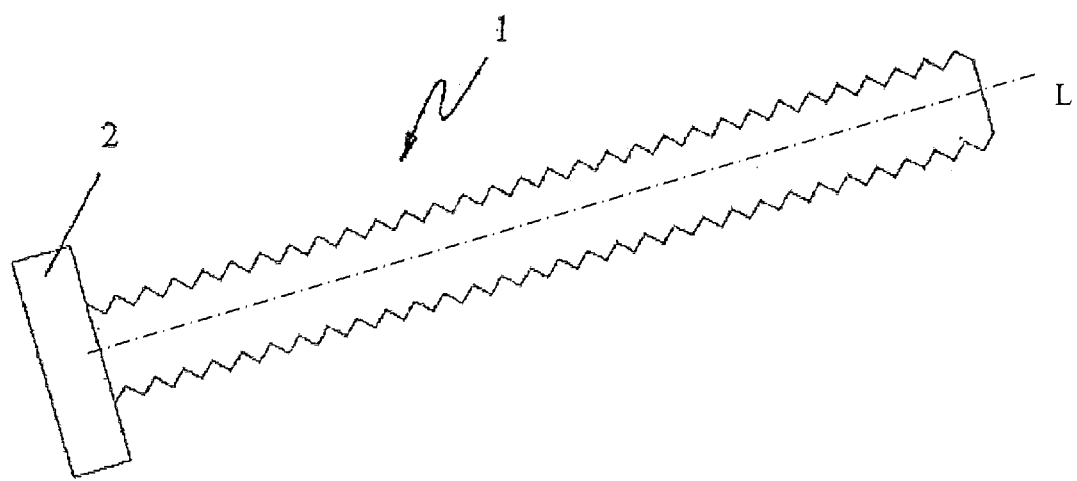
FIG. 1 shows a schematic representation of a bone screw according to the prior art.

The present invention relates to the optimization of bone screws 1 from allogeneic bone, as schematically illustrated in FIG. 1, concerning its properties in the context of operative osteosynthesis, in particular with regard to its fracture strength.

Figure 2:
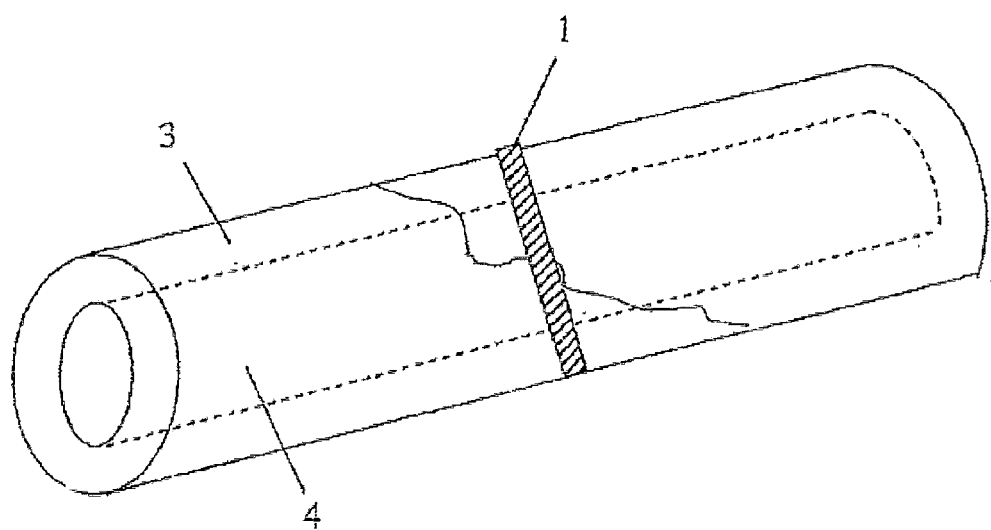
FIG. 2 shows a schematic representation of the fracture site of a bone with an inserted bolt according to the invention in the context of operative osteosynthesis.

For this purpose, bone screws with a symmetrical angular or trapezoidal thread are provided in order not to exert any compression on the bone parts to be connected. In addition, since the strength of the bone joint is essentially dependent on the number of thread turns in the cortical bone 3 of the recipient bone (see FIG. 2), and the contribution of the screw connection along the spongy bone 4 is only small, the bone screws are formed in such a way that they have the highest possible number of thread turns per millimeter along the entire bolt shank in order to ensure that the cortical bone 3 is in connection with a correspondingly high number of thread turns. At a ratio of thread depth to thread diameter between 0.10 and 0.15, a product of this ratio and the number of thread turns per millimeter of 0.10 to 0.30 is provided for this purpose. The symmetrical angular or trapezoidal thread is furthermore guided over the entire length of the bolt shank with a constant thread diameter so that a bone screw 1 is produced as shown in FIG. 1. The bone screw 1 itself can have a square, hexagonal or star head as a screw head 2 (see FIG. 1), which serves merely for the introduction of torque in the course of screwing in, and is cut off after placement of the bone screw 1 so that a configuration according to FIG. 2 is achieved.

In the course of operative osteosynthesis, the fixation and compression of the bone parts to be joined is first ensured by appropriate surgical instruments. Subsequently, a core bore is placed into which a thread is cut. The bone screw 1 according to the invention can now be inserted with a torque wrench, for example, wherein the bone screw 1 traverses the bone parts along the spongy bone 4 and the cortical bone 3 and holds it in a stable state at a predetermined distance without exerting a compression, since a symmetrically designed angular or trapezoidal thread hardly permits tensile loads (see FIG. 2). The bone screw 1 shown therefore does not constitute a tensile screw. However, due to the high number of threads and the associated friction forces, high rotational stability of the bone screw 1 is still provided.

Figure 3:
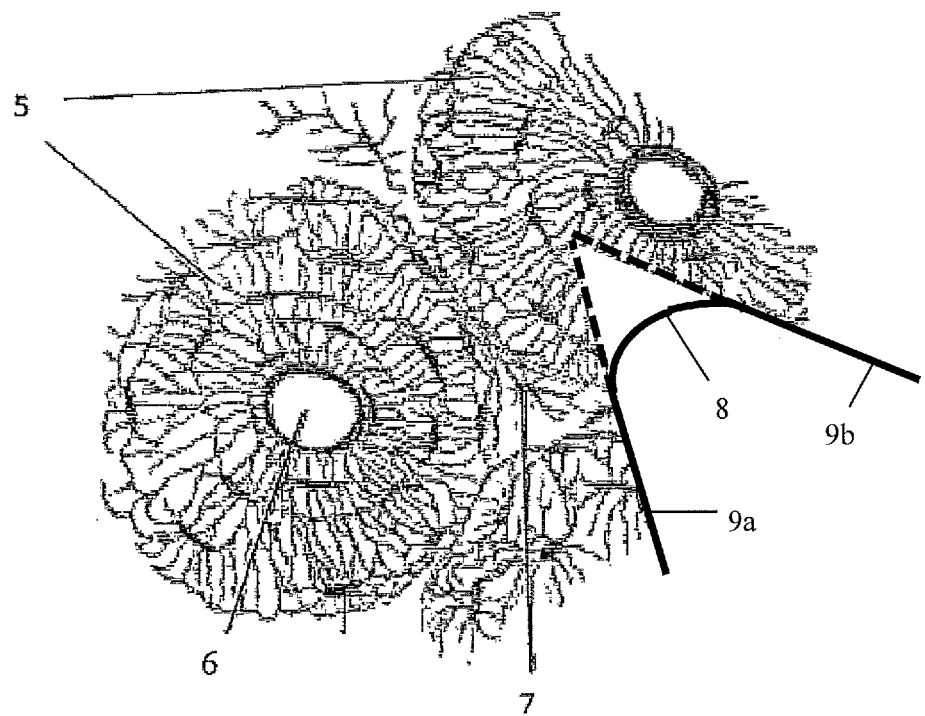
FIG. 3 shows a detail of a cross-section perpendicular to the longitudinal axis of a bone screw for illustrating the structure of an osteon and its Haversian canal as well as the relative position of a thread root portion according to the prior art (dashed line) and according to the invention (continuous line)

For the purpose of explaining the features according to the invention, reference is first made to FIG. 3. FIG. 3 shows a detailed sectional view of a cross-section perpendicular to the longitudinal axis of a bone screw 1 for illustrating the structure of an osteon 5 and its Haversian canal 6 as well as the relative position of a thread root portion 8 according to the prior art (dashed lines) and according to the invention (continuous lines). Since FIG. 3 is a section normal to the longitudinal axis L of the bone screw 1 and is not an axial section, the thread root portion is visible, but no thread root radius can be read. An osteon 5 appears in this section as concentrically arranged lamellae, which are also referred to as specific lamellae, the centrally located Haversian canal 6 and the osteocytes lying between the lamellae. Blood vessels, connective tissue cells and fibers, as well as individual nerve fibers, run in the Haversian canal 6. The individual osteons 5 are, in turn, delimited by so-called intermediate lamellae 7 and connected to each other, wherein the Haversian canals 6 of the individual osteons 5 are connected to each other by transverse canals which likewise contain blood vessels and are also referred to as Volkmann's canals (not shown in FIG. 3).

Osteons 5 and Haversian canals 6 occur only in the cortical bone 3 of long tubular bones, wherein the Haversian canals 6 extend essentially in the longitudinal direction of the donor bone. When the bone screws 1 are cut, the symmetry of the bone structure is conventionally followed and the bone screw 1 is cut in the longitudinal direction of the donor bone so that the longitudinal axis L of the bolt shank extends substantially in the longitudinal direction of the donor bone. Thus, the Haversian canals 6 in the bolt shank of the bone screw 1 also extend substantially parallel to the longitudinal axis L of the bolt shank, as is indicated with reference to FIG. 4.

Figure 4:
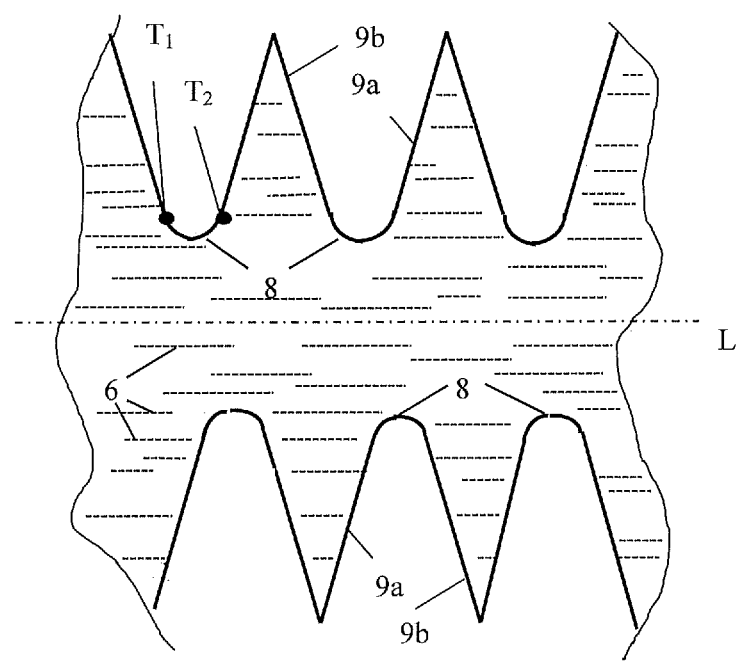
FIG. 4 shows a section of an axial sectional view of a bolt screw according to the invention.

FIG. 4 shows a section of a bone screw 1 according to the invention made from allogeneic, cortical bone material in axial section, i.e. in the longitudinal direction of the cylindrical bolt shank and containing the longitudinal axis L. In FIG. 4, the axes of the Haversian canals 6 extending within the bone material are also shown. FIG. 4 is to be understood schematically and is not true to scale. It also shows an external thread, which is designed as an angular thread, which spirally circulates a cylindrical bolt shank. The symmetrical angular thread has at least one thread turn per millimeter, wherein each thread turn comprises two thread flanks 9a, 9b, which merge into one another via a thread root portion 8. In the exemplary embodiment shown, the transition is implemented without edges, so that the thread flanks 9a, 9b delimiting the thread root portion 8 represent tangents of the adjoining thread root portion 8. The length of the thread root portion 8 can be read in the axial section according to FIG. 4 by the arc length of the thread root portion 8 between the tangential points $T_1$, $T_2$ of the respective thread flank 9a, 9b. According to the invention, this length of the thread root portion 8 which can be read in the axial section of the bolt lies in the range of 0.02 mm to 0.6 mm. If the transition from the thread flanks 9a, 9b to the thread root portion 8 is in each case formed by an edge, the length of the thread root portion 8 is read in axial section by the arc or section length of the thread root portion 8 between the edges.

The lengths of the threaded portion 8 mentioned in the interval provided according to the invention lie in the region of the dimensions of the structural units relevant in the bone material such as such as the Haversian canals 6 and osteons 5, as schematically illustrated in FIG. 3. As already mentioned, the marked increase in the fracture strength is attributed to the fact that the thread flanks 9a, 9b and the thread root portion 8 connecting the thread flanks 9a, 9b intersect the Haversian canals 6 and above all the surrounding osteons 5 with increasingly flat angle, the greater the length of the thread root portion 8. The interval provided according to the invention can be converted in the case of a thread root portion 8, which is designed as an arc of a circle, into thread root radii of approximately 0.01 mm to 0.20 mm, which corresponds to 10 µm to 200 µm. These circular arcs and the thread root radius associated therewith is shown in an axial section according to FIG. 4, wherein, as already stated, FIG. 4 is designed merely schematically and not true to scale. In the mentioned interval of the thread root radii, the corresponding circular arc has in any case a curvature which is comparable with that of the osteons 5, as can also be seen in FIG. 3, which explains the grinding cut. In the event of loading, the pressure acting on the thread flanks 9a, 9b and the thread root portion 8 of the bone screw 1 is thus respectively distributed evenly over the entire tissue of the bone material, i.e. evenly distributed among many surrounding osteons 5. Tensile and compressive loads are thus transferred uniformly and without stress and distributed over a larger area on the bone material. In this way, the exceedingly strong increase in the fracture strength of the bone screw 1 of more than 30% is explained. This makes it possible to use even lower grade, more porous bone material for producing bone screws 1 with equivalent fracture strength.

It is thus possible, with the aid of the invention, to produce bone screws 1 with increased strength so that also less suitable donor material can be used for producing high-quality bone screws 1.

The invention claimed is:

1. A bolt with an external thread and a cylindrical bolt shank of allogeneic, cortical bone material for surgically operative osteosynthesis, wherein the external thread is a symmetrical angular or symmetrical trapezoidal thread with the flank of a thread turn facing the screw-in direction having the same angle as its remote flank, which has at least one thread turn per millimeter, and the bone material is formed by osteons (5) and is permeated by Haversian canals (6), characterized in that thread flanks (9a, 9b), which delimit a thread groove, of the symmetrical angular or trapezoidal thread converge into each other via a thread root portion (8), whose length, in an axial section of the bolt, lies in the range of 0.02 mm to 0.6 mm, and wherein the thread root portion (8) is formed by a circular arc with a thread root radius of 0.01 mm to 0.20 mm.

2. The bolt with an external thread according to claim 1, characterized in that the transition of the thread flanks (9a, 9b) into the thread root portion (8) is arcuate.

3. The bolt with an external thread according to claim 1, characterized in that the thread root portion (8) is formed by a circular arc with a thread root radius of 0.08 mm to 0.20 mm.

4. The bolt with an external thread according to claim 2, characterized in that the thread root portion (8) is formed by a circular arc with a thread root radius of 0.08 mm to 0.20 mm.

5. The bolt with an external thread according to claim 3, wherein the thread root radius is 0.12 mm.

6. The bolt with an external thread according to claim 4, wherein the thread root radius is 0.12 mm.

\* \* \* \* \*